US008012455B2

(12) United States Patent
O'Foghludha

(10) Patent No.: US 8,012,455 B2
(45) Date of Patent: *Sep. 6, 2011

(54) RADIOACTIVE SOURCE MATERIALS FORMABLE INTO VARIOUS SHAPES

(75) Inventor: Fearghus O'Foghludha, Durham, NC (US)

(73) Assignee: Civatech Corporation, Raleigh, NC (US)

(*) Notice: Subject to any disclaimer, the term of this patent is extended or adjusted under 35 U.S.C. 154(b) by 1443 days.

This patent is subject to a terminal disclaimer.

(21) Appl. No.: 11/411,673

(22) Filed: Apr. 26, 2006

(65) Prior Publication Data

US 2007/0081940 A1    Apr. 12, 2007

Related U.S. Application Data

(63) Continuation of application No. 09/614,490, filed on Jul. 11, 2000, now Pat. No. 7,118,729, which is a continuation-in-part of application No. 09/506,611, filed on Feb. 18, 2000, now Pat. No. 6,547,816.

(60) Provisional application No. 60/143,296, filed on Jul. 12, 1999.

(51) Int. Cl.
*A61K 51/00* (2006.01)
*A61N 5/00* (2006.01)

(52) U.S. Cl. ............... 424/1.11; 623/1.15; 600/3; 600/1; 600/7; 600/8; 424/1.25; 424/1.33; 424/1.37; 424/1.65; 424/1.81

(58) Field of Classification Search ........................ None
See application file for complete search history.

(56) References Cited

U.S. PATENT DOCUMENTS

| | | | | |
|---|---|---|---|---|
| 5,079,333 | A | 1/1992 | McGrath et al. | 528/168 |
| 5,163,896 | A | 11/1992 | Suthanthiran et al. | 900/8 |
| 5,407,528 | A | 4/1995 | McGrath et al. | 156/643 |
| 5,691,442 | A | 11/1997 | Unroe et al. | 528/125 |
| 5,993,374 | A | 11/1999 | Kick | 600/8 |
| 6,152,869 | A * | 11/2000 | Park et al. | 600/3 |
| 6,547,816 | B1 * | 4/2003 | O'Foghludha | 623/1.15 |
| 7,118,729 | B1 * | 10/2006 | O'Foghludha | 424/1.11 |
| 2002/0054851 | A1 * | 5/2002 | Grunze et al. | 424/1.81 |

FOREIGN PATENT DOCUMENTS

| | | |
|---|---|---|
| DE | 19754870 | 8/1998 |
| DE | 19953637 | 5/2001 |
| FR | 2230374 | 12/1974 |
| WO | WO91/02766 | 3/1991 |
| WO | WO97/19724 | 6/1997 |
| WO | WO99/39765 | 8/1999 |
| WO | WO00/29034 | 5/2000 |
| WO | WO00/76557 | 12/2000 |

OTHER PUBLICATIONS

Laird, J.R., et al., "Inhibition of Neointimal Proliferation . . .", 1996, Circulation, 93, pp. 1-22.*
Albiero et al., "Short- and Intermediate-Term Results of $^{32}$P Radioactive β-Emitting Stent Implantation in Patients with Coronary Artery Disease," *Circulation*, 101(1): 18-26 (Jan. 4, 2000).
Carter et al., "Current Status of Radioactive Stents for the Prevention of In-Stent Restenosis," *Int. J. Radiation Oncology Biol. Phys.*, 41(1): 127-133 (Apr. 1, 1998).
Cheng et al., "Neutron-Activatable Glass Seeds for Brachytherapy," *Journal of Nuclear Medicine*, 35(5): 242P (Jun. 1994).
Chettle et al., "Techniques of in vivo Neutron Activation Analysis," *Phys. Med. Biol.*, 29(9): 1011-1043 (1984).
Collé, R., "Chemical Digestion and Radionuclidic Assay of TiNi-Encapsulated $^{32}$P Intravascular Brachytherapy Sources," *Applied Radiation and Isotopes*, 50: 811-833 (1999).
European Search Report corresponding to EP03029892 dated Jun. 2, 2004.
Fischell et al., "The Beta-Particle-Emitting Radioisotope Stent (Isostent): Animal Studies and Planned Clinical Trials," *American Journal of Cardiology*, 78(3A): 45-50 (1996).
Hausleiter et al., "A New Phosphorus-32 Balloon Catheter Device for Intracoronary Brachytherapy—Results from the Porcine Stent Model," *Journal of the American College of Cardiology*, 35(2): 51A (Feb. 2000).
Joensuu et al., "Physical and Biological Targeting of Radiotherapy," *Acta Oncologica Suppl.*, 13: 75-83 (1999).
Lansky et al., "Patterns of Intimal Heperplasia after $^{32}$P Brachytherapy: Results from the PREVENT Randomized Clinical Trial," *Circulation*, 100(18): I.222-I.223 (Nov. 2, 1999).
Soloway et al., "The Chemistry of Neutron Capture Therapy," *Chem. Rev.*, 98(4): 1515-1562 (1998).
Wardeh et al., "β-Particle-Emitting Radioactive Stent Implantation," *Circulation*, 100(16): 1684-1689 (Oct. 19, 1999).
Yue et al., "Dosimetry Calculation for a Novel Phosphorus-32-Impregnated Balloon Angioplasty Catheter for Intravascular Brachytherapy," *Cardiovascular Radiation Medicine*, 1(4): 349-357 (1999).
European Exam Report for Application No. 03 029 892.1-1216 dated Apr. 22, 2009.

* cited by examiner

*Primary Examiner* — Michael G Hartley
*Assistant Examiner* — Lance Rider
(74) *Attorney, Agent, or Firm* — Myers Bigel Sibley & Sajovec

(57) ABSTRACT

The present invention provides an integral source material, the integral source material has at least one nuclide that is an integral source material having at least one nuclide that is activatable by exposure to radiation, the nuclide is a chemically bound constituent of a polymer of the integral source material, wherein the integral source material is configured before activation to provide a device.

10 Claims, 1 Drawing Sheet

RADIOACTIVE SOURCE MATERIALS FORMABLE INTO VARIOUS SHAPES

CROSS REFERENCE TO RELATED APPLICATIONS

This application is a continuation of U.S. application Ser. No. 09/614,490, filed Jul. 11, 2000, now U.S. Pat. No. 7,118,729, which application is a continuation-in-part of U.S. application Ser. No. 09/506,611, filed Feb. 18, 2000, now U.S. Pat. No. 6,547,816, which claims the benefit of U.S. Provisional Application No. 60/143,296 filed Jul. 12, 1999, the disclosures of each are hereby incorporated herein by reference.

FIELD AND BACKGROUND OF THE INVENTION

The present invention relates to formable radionuclide sources of beta or gamma radiation, and particularly the use of such sources in industrial or medical devices.

Encapsulated, usually described as "sealed", radionuclide sources of both beta and gamma radiation are widely used in industry and medicine. Typical examples include: (a) sources for thickness gauging, for process control, for weld inspection; for radiation processing and curing, for static electricity elimination and for industrial and medical instrument development, evaluation and calibration; and (b) sources for human radiation therapy by interstitial, intra-cavitary, intra-vascular, and surface methods; for external surface or subsurface irradiation by means of nuclide-bearing applicators; for teletherapy; and for radiation detector adjustment, efficiency determination and other calibration or dosimetric purposes.

The masses, and hence the volumes of radioactive material in many commonly used irradiation devices, are small. For example, the mass of a pure $P^{32}$ sample whose activity is 1 mCi (millicurie) is less than $10^{-10}$ g (grams) and even in the extreme case of $Ra^{226}$ whose atomic mass and half life are large, a 1 mCi sample has a mass of only about 1 mg (milligram). To manufacture sources of customary activities in physical dimensions appropriate to their proposed uses, it is therefore frequently necessary to distribute the active material throughout the volume of, or attach it to the surface of, a non-active matrix or filler of the desired size and shape; the resulting source/filler combination must then be encapsulated or sealed to prevent escape of radioactive material.

Exemplary encapsulation techniques include (1) use of a thin double walled metal container, such as a tube or needle containing the active material in the form of a powder or microbeads, mixed with an inert filler to confer sufficient bulk to fill the container; (2) evaporating a radioactive solution form the surface of the matrix; (3) enclosing an active powder (again accompanied by a volume-augmenting filler) in a thin-walled plastic or metal-foil envelope which is then affixed to a substrate already formed in the desired source shape; (4) impregnating, e.g., a plastic sheet with active material which is mechanically forced into the sheet by a process such as hot rolling; and (5) suspending an already active material in a liquid monomer which is later polymerized in the desired shape. These techniques are particularly difficult to apply when the desired shape is complex; furthermore, the activity distribution achieved may be unacceptably non-uniform and most important, the radiation hazard during manufacture is high.

SUMMARY OF THE INVENTION

To overcome these limitations, the present invention provides an integral source material which uses a polymer base and a nuclide or nuclides that can be activated by exposure to neutrons or other ionizing radiations in order to produce a radioactive material that is chemically integral with and is therefore not easily shed by the polymer base material and that is formable before activation by molding, casting, machining, turning, milling, drilling, grinding or other means such as laser micro-machining. The material, before activation, is formed into some desired configuration, is fabricated into medical or industrial devices and is then irradiated to make the devices radioactive. Activation can be brought about by exposure to neutrons or other ionizing radiation. The resulting post-activation material emits particles, such as electrons or photons, from the chemically-integral nuclides which may be present at high weight fractions. The materials can be fabricated in various shapes and can be further adapted for use post-forming such as by cutting, splicing or combining with other devices. The materials are believed to be relatively safe. The principal advantages of the materials are their formability, the achievable activity levels, the advantageous physical properties such as ruggedness, temperature tolerance, etc., in many cases the biocompatibility of the polymer used, the ease of encapsulating complex configurations, and the greatly reduced hazards of preparation and use.

DETAILED DESCRIPTION OF THE PREFERRED EMBODIMENTS

Figure 1:
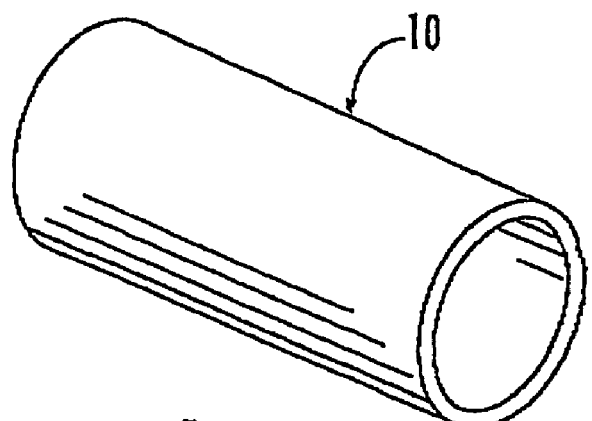
FIG. 1 is a perspective view of an enclosure of the present invention.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

As discussed above, in one aspect the present invention provides an integral source material having at least one nuclide that is activatable by exposure to radiation. The nuclide is a chemically bound constituent of a polymer making up the integral source material.

Any activatable nuclide that can be bound to a polymer is suitable. In general, the nuclide is preferably located in the backbone of the polymer, although side chain configurations are possible. Without being bound by any one theory, it is believed that the backbone configuration results in a more stable integral source material. Typical weight fractions of nuclide in the polymer will be about 1 to 10 percent, although the selection of higher or lower weight fractions will be within the skill of one in the art.

Radiations usable for activating the target nuclide include neutrons and charged particles, for example, protons, deuterons, alpha particles, etc., the selection of which will be within the skill of one in the art. Once activated, the nuclides preferably emit β or γ radiation or x-rays or combinations thereof. The attainable activity can range from microcuries (μCi) to millicuries (mCi). The activity reached depends on the nature and isotopic abundance of the target nuclide, its activation cross-section, the flux of activating radiation, the irradiation time, half-life and certain other properties.

As stated above, various nuclides that can become a chemically bound constituent of any polymer can be used. Suitable nuclides include, but are not limited to the following: Li, Na, C, F, Al, P, S, Cl, Ca, Ti, V, Cr, Mn, Fe, Co, Ni, Cu, Zn, Ge, Sr, Y, Zr, Mo, Tc, Rh, Pd, I, Cs, Ba, La, Ce, Eu, Gd, Re, Ir, Au, Hg, Pb, Bi, Po and Am. Combinations of such nuclides can be used; for example, a nuclide with a short half-life may be used in combination with one having a longer half-life. Suitable polymers include, but are not limited to the following: polypropylene, polyethylene terephthalate, nylon, acrylates, polyurethane, polyphenylene oxide blends, polyphenylsulfone, polysulfone, polyether sulfone, polyphenylene sulfide, phenyletheretherketone, polyetherimide, polyphenylmetalosiloxane, fluorine-containing polyphosphazines and liquid crystal polymers.

The present invention provides target species whose concentration is of necessity perfectly uniform because of the role of the target atom as a molecular constituent of the matrix. Some spatial variation in the final radioactivity may remain in spite of the uniform target-atom distribution but this variation is due to non-uniform distribution of the activating flux before it strikes the irradiated object and subsequent absorption of the flux as it penetrates the target. However, non-uniformity can be minimized by assembling a large area from an array of smaller and identically active pieces, i.e., by "tiling."

Industrial and medical devices of almost any shape can be fabricated while the target material is still inert, without external or internal radiation hazard, and without contaminating the molds or tools used in forming. Some examples of devices that can be fabricated by means of the invention are:

(a) Stents, seeds, catheters, irradiator tubes, applicators and molds, enclosures, shrouds, ribbons, rods, beads, needles, obturators discs and the like and combinations thereof such as described in U.S. patent application Ser. No. 09/506,611 filed Feb. 18, 2000. An exemplary stent 10 is shown in FIG. 1.

(b) Test-objects. Test objects, such as one example, a miniature checkerboard, consisting of alternating active and inactive squares, are easily made from invention materials. The squares, the proposed active ones of which contain target nuclides while the proposed inactive ones do not, are assembled while still inactive, i.e. without hazard, and the whole is then exposed to the activating agent, resulting in a checkerboard or other complex-patterned test-object which can be used to determine the resolving power of autoradiographic emulsions or other high spatial resolution detectors. Larger objects, e.g. bar-charts or similar test objects, can be fabricated for calibration, e.g., of gamma cameras.

(c) Large area sources. In some thickness gauging applications, for example in automatic on-line quality control in the manufacture of sheeting or textile fabrics, rectangular sources are often used whose longer sides equal or exceed the width (often considerable) of the material under test; those sources that rely on beta-emitters, whether of the pure beta or beta-gamma type, present a difficult encapsulation problem because the sealing must be rugged enough to resist puncture in an industrial environment but must be simultaneously thin enough to permit adequate passage of the particles whose transmission through the material being inspected is a measure of absorber thickness. Suitable sources are easily fabricated from slabs of unactivated integral source material fabricated to the proper dimensions by molding or machining, after which the target atoms are activated by exposure to neutrons or other activating fluxes. This relatively safe and convenient operation is in contrast with the conventional method of manufacture in which an already radioactive and thus hazardous material must first be uniformly distributed on and then uniformly affixed to a substrate of the required shape before encapsulation in situ. Using invention materials, the discs can be encapsulated before activation by dipping in or otherwise coating with a non-activatable polymer.

(d) Radioactive Enclosures. Invention materials may be used to fabricate enclosures with radioactive walls as a means of irradiating target objects placed within the enclosures. Depending on the nature ($\beta$, $\gamma$ or ($\beta$+$\gamma$)) of the radiations emitted from the walls, the phase (i.e., sold or liquid) and the dimensions and absorbing properties of the targets, the enclosure can be in the form of rigid or flexible tubing of internal diameters as small as a few mm, or in shapes which tightly invest objects of quite irregular form such as electronic components, or as spheres, ellipsoids or cylinders of large dimensions (tens of cm). Radioactive tubing made from invention materials may be used, as an example, to irradiate flowing blood in the technique known as human extra-corporeal irradiation (ECI), where blood from a living subject is passed through an external irradiator and is than continuously returned to the subject's vascular circulation. The tubing walls may emit $\gamma$ radiation, with the disadvantages that energy-transfer to the flowing blood is small and that the irradiator must be heavily shielded; or alternatively, the wall emission may consist only of $\beta$ particles, with the advantage that energy transfer is very efficient and shielding requirements are minimal. If non-radioactive tubing is used, as in existing ECI devices, the sources must be outside the tubing, which interposes absorbing material, i.e., the tube wall, between the sources and the target liquid within the tube; use of active tubing made from invention material eliminates this disadvantage. A further use of the invention material in ECI is construction of radiating manifolds to maximize the volume of blood instantaneously present in the irradiator. Increasing the cross-section of the tubing that delivers blood to the device is unsatisfactory because $\beta$-rays from the walls then heavily irradiate liquid elements near the walls while elements nearer the axis receive a smaller dose or none at all, depending on the $\beta$-energy and the tube diameter. This can be avoided by carrying the blood in a large-diameter tube to the plenum of a manifold where it is divided among multiple radiating channels each of sufficiently small diameter to guarantee adequate energy deposition at their axes.

(e) Flood sources. Flood sources used in nuclear medicine quality control, e.g., in evaluation of gamma-camera responses, are a special type of large area source. They are usually in the form of thin discs, typically from about 30 up to about 60 cm in diameter or rectangles of approximately equivalent areas. The flood sources are sometimes in the form of shallow closed but re-fillable tanks containing a radioactive liquid. This approach guarantees the constancy of the activity per unit volume but has the disadvantage that handling radioactive liquids is hazardous. Flood sources are also made by mechanically admixing a small volume of radioactive solution into a suitably-shaped mass of uncured epoxy resin which is then cured to a solid form. Sources made by admixture of already active material must be checked for non-uniformity before first use. This is because the highly viscous nature of the uncured epoxy hinders uniform mixing. Sources made from invention materials on the other hand have absolutely uniform concentration of active materials provided the flux required to activate the target is uniform over the area of the flood source. However, very large sources may be readily assembled to form a mosaic by juxtaposing a number of segments ("tiles") each of which is smaller than the area over which the activating flux is acceptably constant. The active nuclide in current flood sources is usually $^{57}Co$, which can be produced in, for example, the reactions: $^{58}Ni(\gamma,p)^{57}Co$, $^{56}Fe(p,\gamma)^{57}Co$, $^{56}Fe(d,n)^{57}Co$, and $^{55}Mn(\alpha 2n)^{57}Co$. These reactions are also usable in fabricating sources for x-ray fluorescence analysis described below.

(f) Nuclear imaging devices. For example, rigid rod-like sources used in measuring line-spread functions by methods known to those in the art may be fabricated from the integral source material of the invention. Yet other uses are the creation of resolving-power test arrays in a grating-like pattern of parallel line sources separated by inactive i.e. non-radiating members; such patterns may be made for autoradiographic measurements in micro- as well as the more usual macro-patterns used in testing nuclear medicine and similar instrumentation.

(g) Radiation curing for protective shrouds. Another use of invention materials is the production of sources useful in the radiation curing (i.e., hardening) of protective shrouds. A shroud is a thin protective layer, usually of a polymeric substance, covering the entire surface of, as one example, an electronic circuit board carrying irregularly shaped resistors, capacitors, chips and the like. Curing to confer hardening is often carried out at very high dose rates, by means of a "bath" electron beam or a similar small-area scanning beam, but even when the object is rotated under the beam, the multiply-reentrant surfaces exercise a complex shielding effect on different parts of the shroud with the result that curing success is spotty. Using invention materials, intimate contact is maintained between the irradiator and the layer that is to be cured, ensuring uniform curing and ensuring a high dose-rate. The technique is advantageous where low-throughput curing of highly valuable objects, such as custom-built circuit boards, is the goal. The largest enclosures, in the form of right circular cylinders of up to 50 cm or thereabouts in diameter, and of approximately the same length, are capable of irradiating the surfaces (if β-emitting invention materials are used) and/or the entire volume (with γ emitters) of e.g., the human body. In these applications, the very large radiating area can be assembled by tiling, as before, with the difference that exact equality of emission at each point on the irradiator surface is not so critically important as making flood sources for gamma cameras, where operators often demand areal constancy to within about ±1%.

(h) Excitation sources for x-ray fluorescence analysis. Another example of the use of integral source material is in fabricating sources for energy-dispersive x-ray fluorescence (XRF) studies. XRF is a technique well known to those in the art for qualitative and quantitative analysis of samples for environmental, forensic and other purposes. The procedure requires the use of an exciting source whose emitted photons excite fluorescent x-rays in the sample under analysis. Energy-dispersive examination of these fluorescent x-rays serves to detect the presence and determine the amounts of various fluorescing species in the sample under examination. The XRF excitation sources are often supplied in either annular or disc geometries. The invention materials can be used to produce both types, with the significant advantage over current sources that the invention material source need not be encapsulated in sealed containers; this difficult process involves the need to weld or otherwise seal already active material in a capsule that has a window (often made of Kapton, beryllium, stainless steel, aluminum or some other material); in addition, the window attenuates the source photons, particularly for low energy sources such as $^{55}Fe$.

Excitation-source materials containing $Co^{57}$ can be produced by the reactions already listed in section (e) above, using poly(phenylmetallosiloxane)s that contain $^{58}Ni$, $^{56}Fe$ or $^{55}Mn$ as target materials, while the same or other polymers containing $^{54}Fe$ as target atoms can be activated via the reaction $^{54}Fe(n,\gamma)^{55}Fe$.

Figure 2:
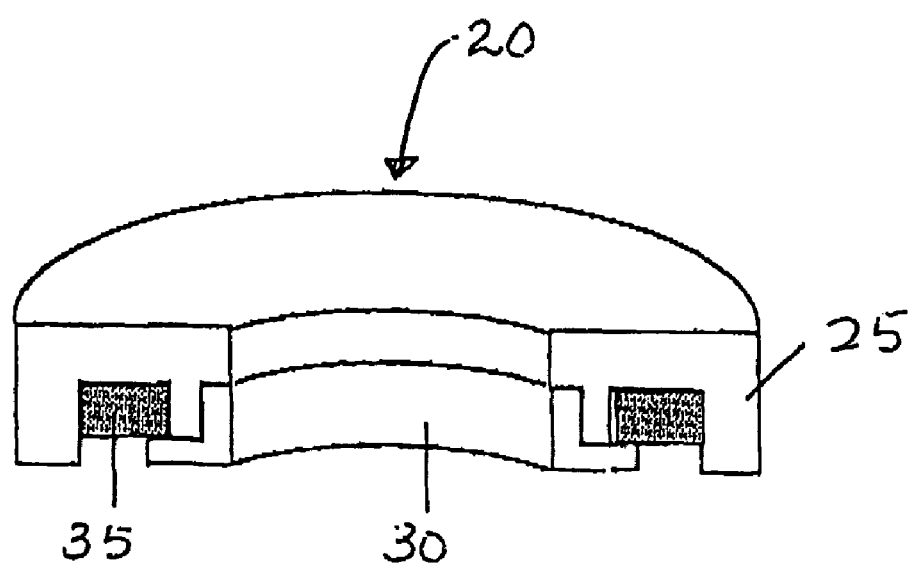
FIG. 2 is a perspective view of an x-ray fluorescence excitation source of the invention.

A preferred embodiment of an annular XRF excitation source made of integral source material is indicated in FIG. 2. A suitable polymer that contains $^{58}Ni$, $^{56}Fe$, or $^{54}Fe$ is formed into an annular ring 20 having dimensions typically of the order of 0.5 to 1 inch interior diameter, 0.75 to 1.25 inch outer diameter and thickness 0.1 to 0.3 inch. The forming process takes place prior to irradiation while the integral source material of the invention is non-radioactive. A shielding holder 25 made of tungsten, brass or other material (for shielding in desired dimensions) and a retainer ring 30 are made to accommodate the integral source material ring 35. The ring 35 is irradiated in a gamma, charged particle, or neutron environment to produce the desired excitation source ($^{57}Co$ or $^{55}Fe$), placed in the shielding holder, and fixed in place with the retainer ring, which can be press fit, glued, welded, or otherwise attached.

In one embodiment of the invention the mesh is fabricated from threads or strands of the base polymer polyarylene ether phosphine oxide which contains as target substance about 9.7% by weight of phosphorus 31, whose isotopic abundance is 100%. On exposure to thermal neutron radiation the target i.e., initially inactive phosphorus 31 is activated and becomes phosphorus 32, a pure β-emitter with maximum energy of about 1.72 MeV and half life of about 14 days; none of the other constituents of the base polymer is activated. The phosphorus is substantially chemically contained in the mesh material. Because of the high concentration of phosphorus in the base polymer the material can if desired be activated to a saturation specific activity of about 10 mCi per gram of polymer by exposure to thermal neutron fluence rates that are readily produced by typical nuclear reactors.

That which is claimed is:

1. A method of forming an integral source material comprising:
providing an integral source material comprising a polymer chain having at least one non-radioactive nuclide that is activatable by exposure to radiation and is a chemically bound constituent of the backbone of the polymer of the integral source material;
forming the integral source material into a device, wherein the device is selected from the group consisting of test-objects, rectangular and disc shaped sources configured to radiate an area, radioactive enclosures, flood sources, nuclear imaging devices, shrouds and excitation sources for energy-dispersive fluorescence analysis; and
exposing the integral source material to radiation to activate the at least one nuclide of the polymer chain, wherein the device comprises a checkerboard pattern comprising alternating active and inactive squares, the active squares containing the integral source material.

2. The method of claim 1, wherein exposing the integral source material to radiation comprises exposing the integral source material to neutrons.

3. The method of claim 1, wherein the polymer is selected from the group consisting of polypropylene, polyethylene terephthalate, nylon, acrylates, polyurethane, polyphenylene oxide blends, polyphenylsulfone, polysulfone, polyether sulfone, polyphenylene sulfide, phenyletheretherketone, polyetherimide, polyphenylmetallosiloxane, fluorine containing polyphosphazenes and liquid crystal polymer and blends and combinations thereof.

4. The method of claim 1, wherein the nuclide is selected from the group consisting of one or more of Li, Na, Al, P, S, Ca, Ti, V, Cr, Mn, Fe, Co, Ni, Cu, Zn, Ge, Sr, Y, Zr, Mo, Tc, Rh, Pd, Cs, Ba, La, Ce, Eu, Gd, Re, Ir, Au, Hg, Pb, Bi, Po and Am.

5. The method of claim 1, wherein the device comprises a rectangular substrate for irradiating an area.

6. The method of claim 1, wherein the device comprises a tube enclosure having radioactive walls.

7. The method of claim 6, wherein the tube enclosure comprises a flexible material.

8. The method of claim 6, wherein the tube enclosure comprises a rigid material.

9. The method of claim 1, wherein the polymer further comprises a side chain comprising a second nuclide consisting of I, F or Cl.

10. The method of claim 1, wherein the polymer further comprises a side chain comprising a second nuclide consisting of I, F or Cl.

* * * * *